United States Patent [19]
Kobayashi et al.

[11] Patent Number: 5,444,504
[45] Date of Patent: Aug. 22, 1995

[54] OPTOMETRIC APPARATUS

[75] Inventors: Toshiro Kobayashi, Anjo; Kazuhiro Yoshimura, Toyohashi; Akihiro Hayashi, Toyokawa; Yoshinobu Hosoi, Gamagori; Nobuyuki Yano, Okazaki, all of Japan

[73] Assignee: Nidek Co., Ltd., Japan

[21] Appl. No.: 18,033

[22] Filed: Feb. 16, 1993

[30] Foreign Application Priority Data

Feb. 21, 1992 [JP] Japan ................................. 4-072313
Sep. 30, 1992 [JP] Japan ................................. 4-287002

[51] Int. Cl.⁶ .............................................. A61B 3/02
[52] U.S. Cl. ........................................ 351/237; 351/243; 351/244; 351/245
[58] Field of Search ............... 351/215, 220, 222, 232, 351/237, 239, 243, 244, 245

[56] References Cited

U.S. PATENT DOCUMENTS

| 4,298,253 | 11/1981 | Tagnon | 351/222 |
| 4,753,527 | 6/1988 | Ishihara | 351/244 |

FOREIGN PATENT DOCUMENTS

| 0229570 | 7/1987 | European Pat. Off. |
| 2461316 | 1/1981 | France. |
| 853329 | 7/1949 | Germany. |
| 3444580 | 6/1986 | Germany. |
| 4-347125 | 2/1992 | Japan. |

*Primary Examiner*—William L. Sikes
*Assistant Examiner*—David R. Parsons
*Attorney, Agent, or Firm*—Parkhurst, Wendel & Rossi

[57] ABSTRACT

An optometric apparatus includes an operating table and a vision test chart displaying device provided internally within the operating table. An optical group, including a plurality of reflection-type optical elements, are disposed within the operating table. The optical group repeatedly reflects an optical image of the vision test chart projected from the vision test chart displaying device along an optical path within said operating table. A first deflecting optical element reflects the optical image of the vision test chart reflected by the reflection-type optical element group outside the operating table in a first direction. A second deflecting optical element then reflects the optical image of the vision test chart reflected by the first deflecting optical element in a second direction toward the examinee's eyes. A line of vision of the examinee in looking at the optical image reflected by the second deflecting optical element obliquely intersects a plane passing through the optical path defined by the optical group.

14 Claims, 23 Drawing Sheets

FIG. 4 (a) PRIOR ART
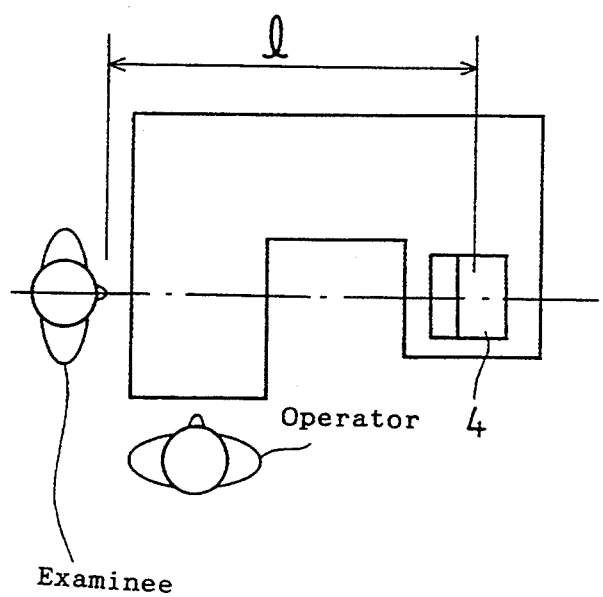
FIG. 4 (b)
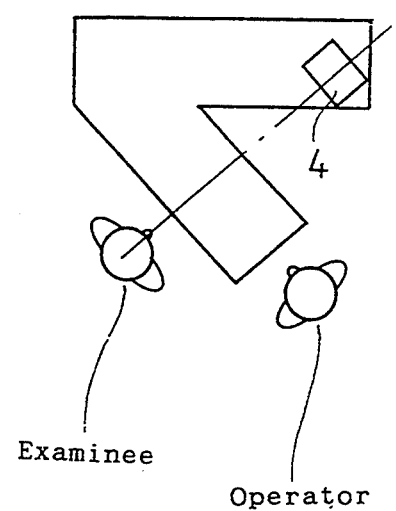
FIG. 4 (c) PRIOR ART
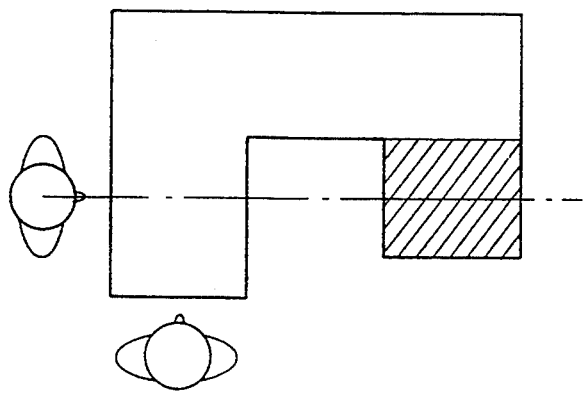

FIG. 5 (a) PRIOR ART
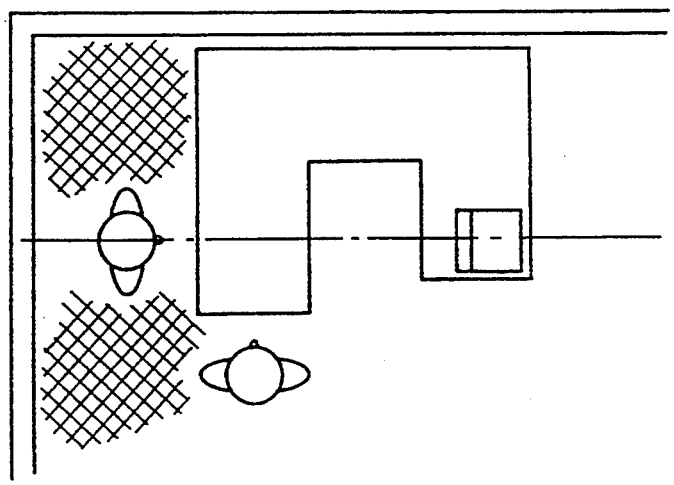
FIG. 5 (b)
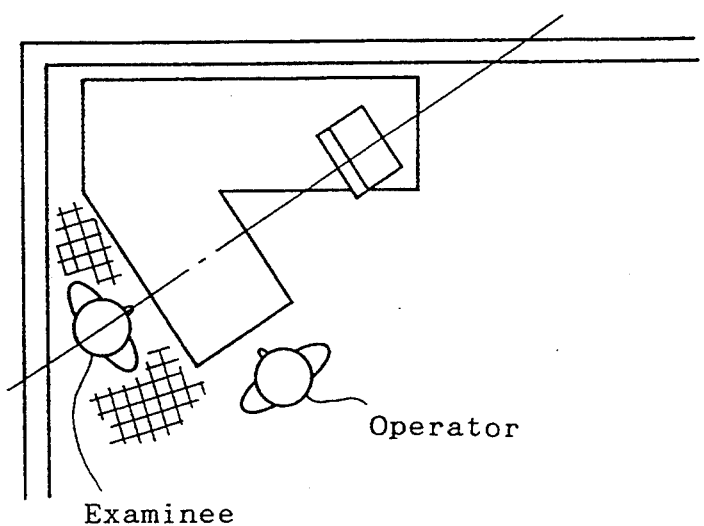

FIG. 6 (a) PRIOR ART
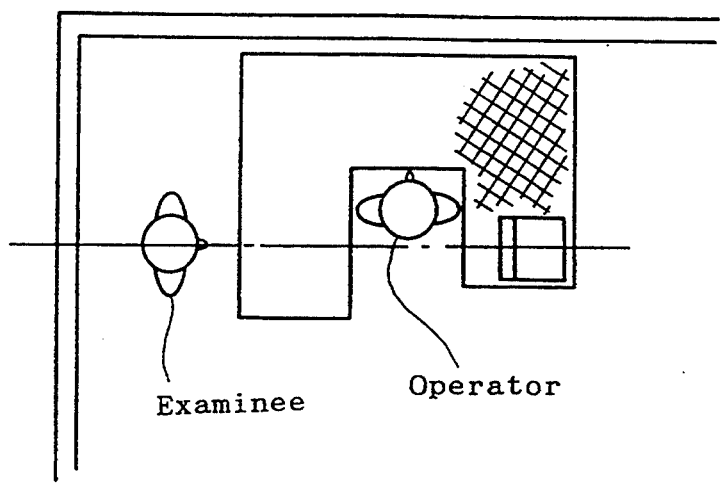
FIG. 6 (b)
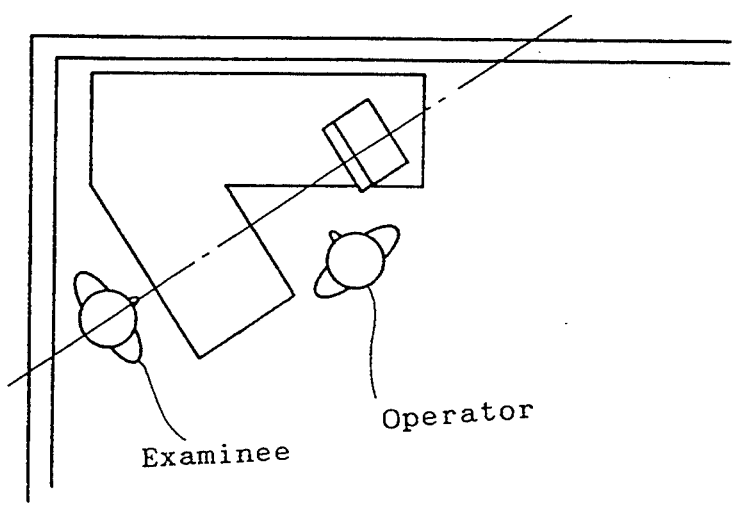

FIG. 7 (a) PRIOR ART
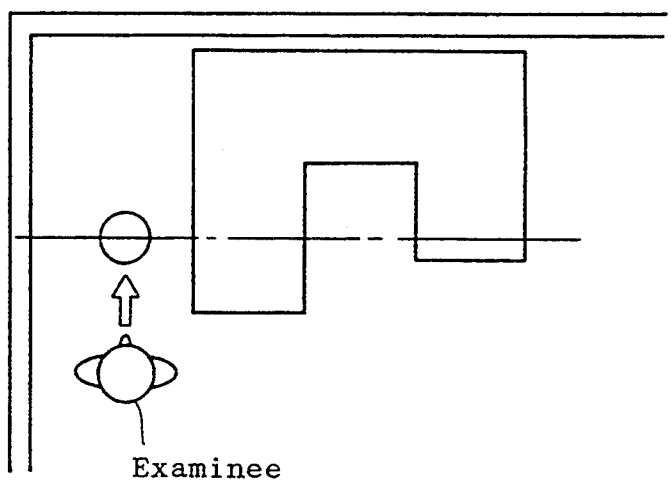
FIG. 7 (b)
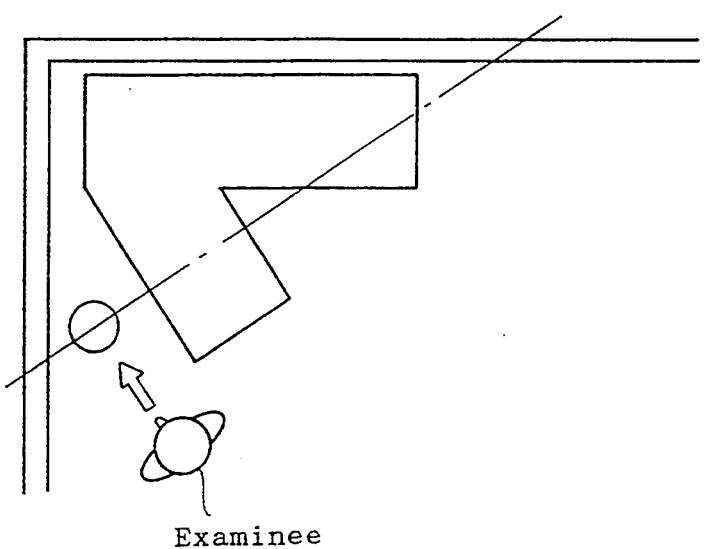

FIG. 21 (a)
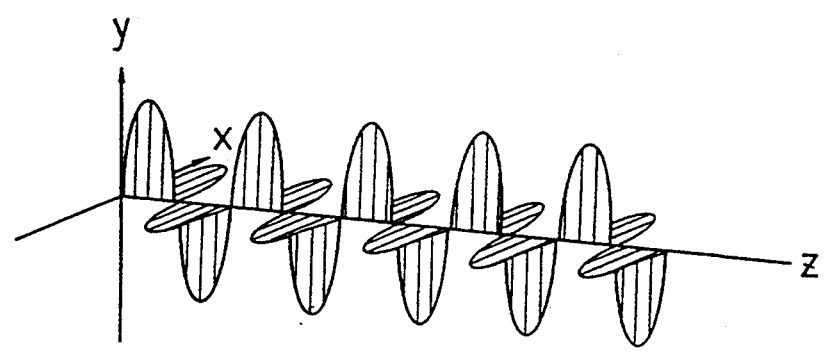
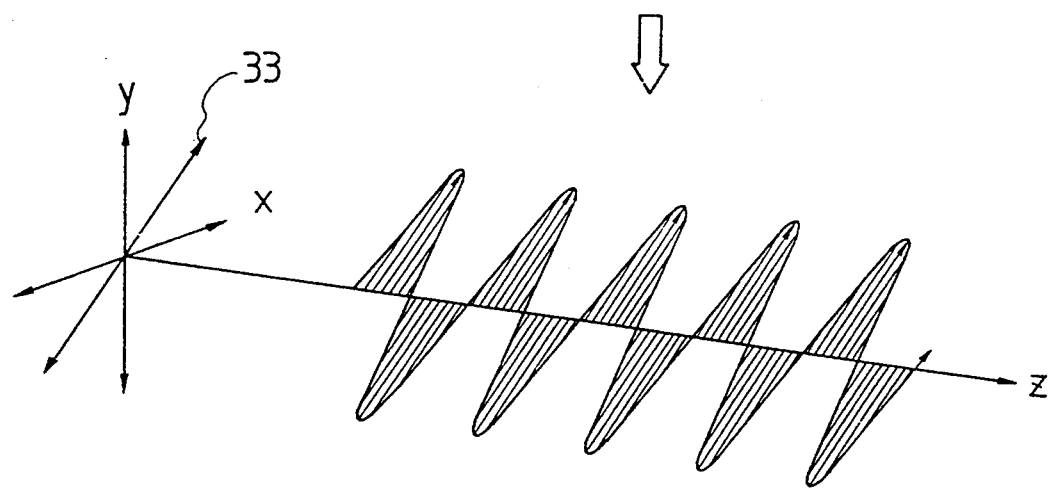
FIG. 21 (b)

OPTOMETRIC APPARATUS

BACKGROUND OF THE INVENTION

1. Field of the Invention

The present invention relates to an optometric apparatus for a visual acuity test, and more particularly to an optometric apparatus of table type provided with an internal vision test chart displaying device, and further to a suitable apparatus for confirming a polarized vision chart through a polarizing plate disposed opposite to the examinee's eyes.

2. Description of Related Art

Generally, a vision test chart to be placed at a vision testing distance 5 m from the examinee's eye is used for a visual acuity test, that is, the vision test chart of a direct display type should be disposed actually at a position 5 m apart from the examinee's eyes. However, effectively utilizing the space of a shop is demanded in an optician's shop or the like, therefore, there are known vision testers of reflection display type using reflecting mirrors to display a vision test chart at a virtual vision testing distance, which is shorter than the actual vision testing distance from the examinee's eye.

A vision tester requiring less space was proposed previously by the applicant of the present patent application in Japanese Patent Application No. HEI 3(1991)-144904 contains a vision test chart projector in the operating table, requiring a smaller space. In this vision tester, the optical image projected by the vision test chart projector is reflected repeatedly by plural mirrors contained in the operating table so as to travel toward the outside of the operating table and reflect the optical image toward the examinee's eye by a last mirror disposed in a front of the examinee's eye. More specifically, the mirrors arranged within the operating table comprises plural mirror groups for reflecting the optical image repeatedly to increase the optical distance between the examinee's eyes and the optical image of the vision test chart to the vertical vision testing distance, and a deflecting mirror for reflecting the optical image toward the last mirror disposed in a front of the examinee's eye. After reflected repeatedly by plural mirror groups, the optical image of the vision test chart is reflected by a deflecting mirror toward a last mirror, and traveled to the examinee's eye. By using such vision tester, a space between the optical image of the vision test chart and the examinee's eye is reduced, therefore, the vision testing may be executed in a smaller space.

Another vision tester requiring a smaller space for vision testing has a test chart projector provided in a box (an operating table in the present specification includes the box) placed beside an operating table, reflects the optical image of a vision test chart repeatedly and guides the optical image from the position above the examinee to a mirror disposed opposite to the examinee to reflect the optical image toward the examinee's eye. In this vision tester, the optical path comprises the almost same fundamental construction in a plan view as that of the above mentioned vision tester.

As mentioned above, the latter vision testers needs a smaller space for its establishment than the former providing an operating table separately from a test chart projector.

However, the vision testers comprising plural mirrors need a relatively large table for considering a space reduced because of reflecting mirror system, and it is difficult to zoom the optical image of a vision test chart for far vision testing and near vision testing selectively in a vision test with a trial lens because a distance between the examinee's eye and a last mirror to reflect the optical image toward the examinee's eye is not enough.

Additionally, when the incident and reflecting plane is changed greatly by reflected through a mirror, the optical image may not disappear even if the polarizing axis of the polarizing vision chart intersects the polarizing axis in the examinee's eye side, thereby some problems may occur in a functional test through the binocular vision, for example that the examinee is unable to find clearly only the optical image for a visual acuity test of one eye, right or left.

SUMMARY OF THE INVENTION

The present invention has been made in view of the above circumstances and has an object to overcome the above problems and to provide a table-type optometric apparatus comprising a vision test chart displaying device capable of zooming the optical image of a vision test chart for far vision testing and near vision testing in preferable condition for the examinee and further in a small space for vision testing.

Another object of the present invention is providing an optometric apparatus capable of displaying a polarizing vision chart in good appearance by reflecting mirrors, whereby an exact polarizing visual test may be achieved.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, an optometric apparatus of this invention comprises an operating table, a vision test chart projecting device provided internally with the the operating table, plural reflection-type optical element groups disposed in the operating table to reflect repeatedly an optical image of the vision test chart projected from the vision test chart projecting device, a first deflecting optical element for deflecting the optical image of the vision test chart reflected by the reflection-type optical element groups toward another direction, a second deflecting optical element for reflecting the optical image of the vision test chart reflected by the first deflecting optical element toward the examinee's eyes, and the line of vision of the examinee in looking at optical image on the second deflecting optical element intersect an optical path defined by the reflection-type optical element obliquely.

Further, in another aspect of the present invention, an optometric apparatus comprises a vision test chart projecting device for projecting an optical image of a vision test chart, a first deflecting optical element for reflecting the optical image of the vision test chart projected from the vision test chart projecting device, a second deflecting optical element for reflecting the optical image of the vision test chart reflected by the first deflecting optical element toward the examinee's eyes, the second deflecting optical element having an incident plane which is not in the same plane as an incident plane of the first deflecting optical element, a polarizing plate arranged on the optical path to transmit the optical image of the vision test chart projected from the vision test chart projecting device toward the examinee's eyes, and control means for controlling an angle of the polarizing axis of the optical image of the vision test chart projected from the vision test chart projecting device and an angle of the polarizing light axis of the polarizing plates according to an angle between an incident plane of the first deflecting optical element and that of the second deflecting optical element, and according to each incident angle to the first deflecting optical element and to the second deflecting optical element.

The optometric apparatus of the present invention needs a relatively small space for testing operation, is accessible equally to the conventional optometric apparatus having a test chart display unit and an operating table, which are installed separately, and whereby the examinee is able to watch the optical image of a vision test chart comfortably in a visual acuity test.

Further, the optometric apparatus of the present invention, compared with a conventional table-type optometric apparatus containing a vision test chart displaying device, requires a smaller space for its establishment, and has a simple construction, accordingly the applicability of the optometric apparatus for the visual test may become wider.

Further, because a necessary space for the visual test can be reduced, another many apparatus may be installed in the oculist's consulting room, and the consulting room itself may be reduced in size. Similarly, because of a smaller space for visual test, many goods like glass frames can be displayed in the optician's store, and its store area may be reduced.

As an optometric apparatus being compact, it is possible to reduce a cost of an apparatus itself, and to supply the optometric apparatus at low price on the market, further to carry it in or out easily.

In the present invention, changing a combination of angle of polarizing axis of a vision test chart displaying device and the same in the examinee side can dissolve problems of polarizing vision chart displayed on a last mirror caused by arranging reflecting mirrors between a vision test chart and the examinee, therefore, the binocular functional test may be executed comfortably.

Furthermore, since the mirrors of the optometric apparatus of the present invention are driven automatically, the measurement of the visual power can be readily achieved. The optometric apparatus of the present invention enables the examinee to watch the optical image of a vision test chart in a natural position regardless of the size of the trunk and makes the examinee neither uneasy nor unpleasant.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention. In the drawings.

FIG. 4(a) through FIG. 4(c) are schematic plan views comparing an optometric apparatus according to the present invention and a conventional apparatus, that is, (a) is a schematic plan view showing a conventional optometric apparatus, (b) is a schematic plan view showing an optometric apparatus according to the present invention, and (c) is a schematic plan view showing an excessive space indicated by oblique line in a conventional optometric apparatus compared with an optometric apparatus of the present invention shown in FIG. 4(b);

FIG. 5 (a) and (b) are schematic plan views showing respective dead space occurred when these optometric apparatus of FIG. 4 (a) and (b) are disposed in the corner of a room respectively;

FIG. 6 (a) and (b) are schematic plan views showing respective dead space on tables of optometric apparatus FIG. 4 (a) and (b);

FIG. 7 (a) and (b) are schematic plan views explaining the convenience for the examinee of going in and out the corner of the room in which a conventional optometric apparatus (a) and an optometric apparatus of the present invention (b) are respectively arranged as shown in FIG. 5;

FIG. 21 is a diagrammatic view of explaining an general conception of the polarized light;

DETAILED DESCRIPTION OF THE PREFERRED EMBODIMENTS

A detailed description of one preferred embodiment of an optometric apparatus embodying the present invention will now be given referring to the accompanying drawings.

Figure 1:
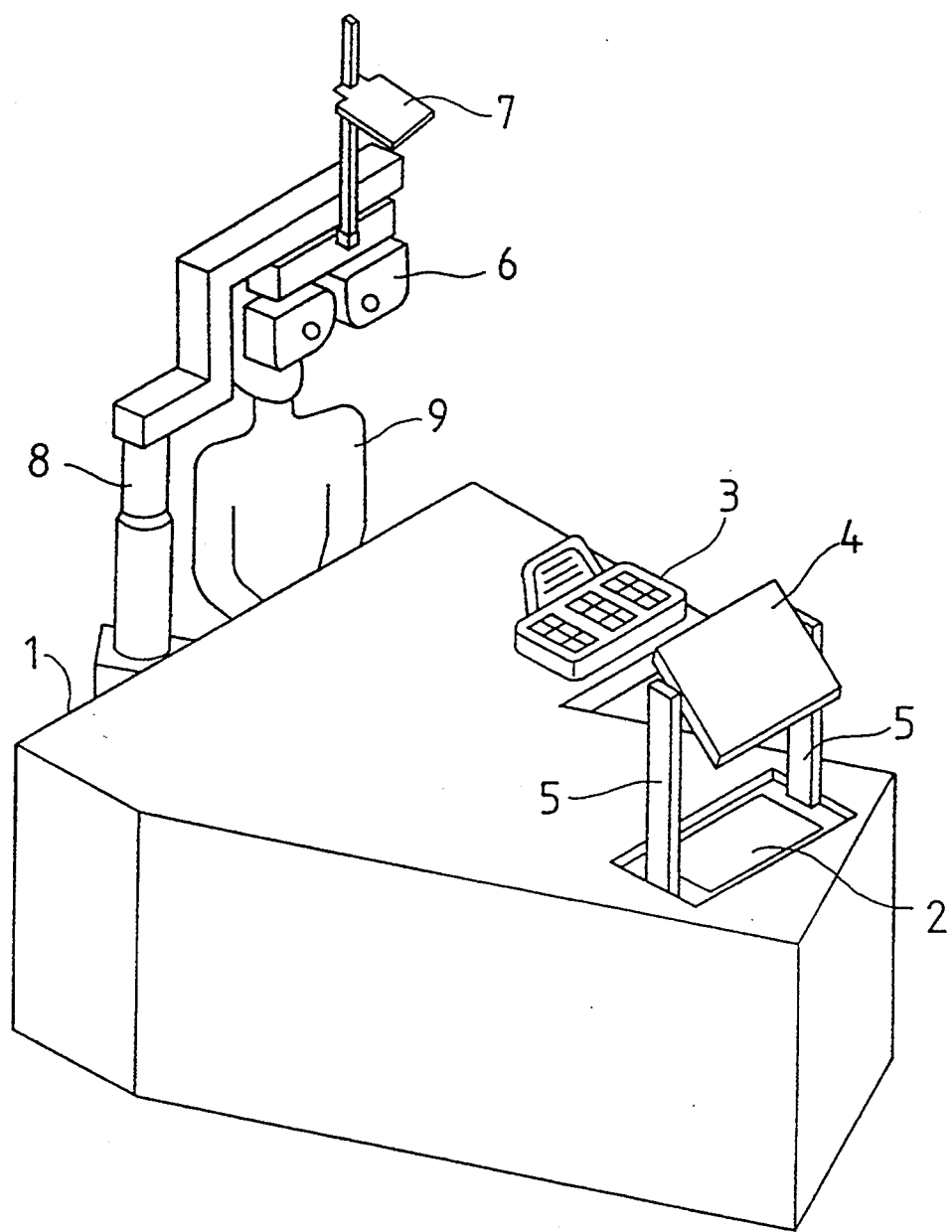
FIG. 1 is a perspective view of an optometric apparatus in a first embodiment according to the present invention.
Figure 2:
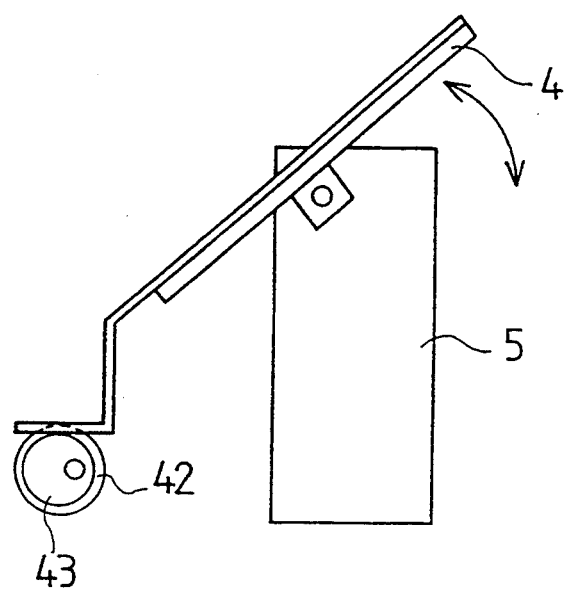
FIG. 2 is an enlarged diagrammatic view of the reflecting mirror rotating mechanism shown in FIG. 1.

FIG. 1 shows an optometric apparatus in a first embodiment according to the present invention. Referring to FIG. 1, an operating table 1 is provided internally with a test chart projecting unit (chart projector) and a reflecting mirror unit for reflecting the optical image of a vision test chart projected by the test chart projecting unit. The optical image of the vision test chart travels outside the operating table 1 through a glass window 2. A subjective refractor 8 and the test chart projecting unit are operated by the examiner by operating a controller 3 provided with operating keys. A mirror 4 for reflecting the optical image toward the examinee's eye is supported pivotally on a pair of support posts 5. The inclination of the mirror 4 can be changed by a turning mechanism formed in the support posts 5. The distance between the mirror 4 and the examinee is 100 cm. FIG. 2 shows one embodiment of the turning mechanism for turning the mirror 4. In brief, the mirror 4 is fixed to a support post 5 pivotally in the direction of the arrows in this FIG. 2 with an eccentric cam 43 which is turned by mirror turning motor 42.

A near vision test chart 7 is supported on the subjective refractor 8 which may provide selectively the optical element having various character on a vision test window. Preferably, the distance between the examinee and the mirror 4 is not less than 70 cm. The subjective refractor 6 is supported on a telescopic support post 8, which is able to turn about the axis and to be extended or contracted.

Figure 3:
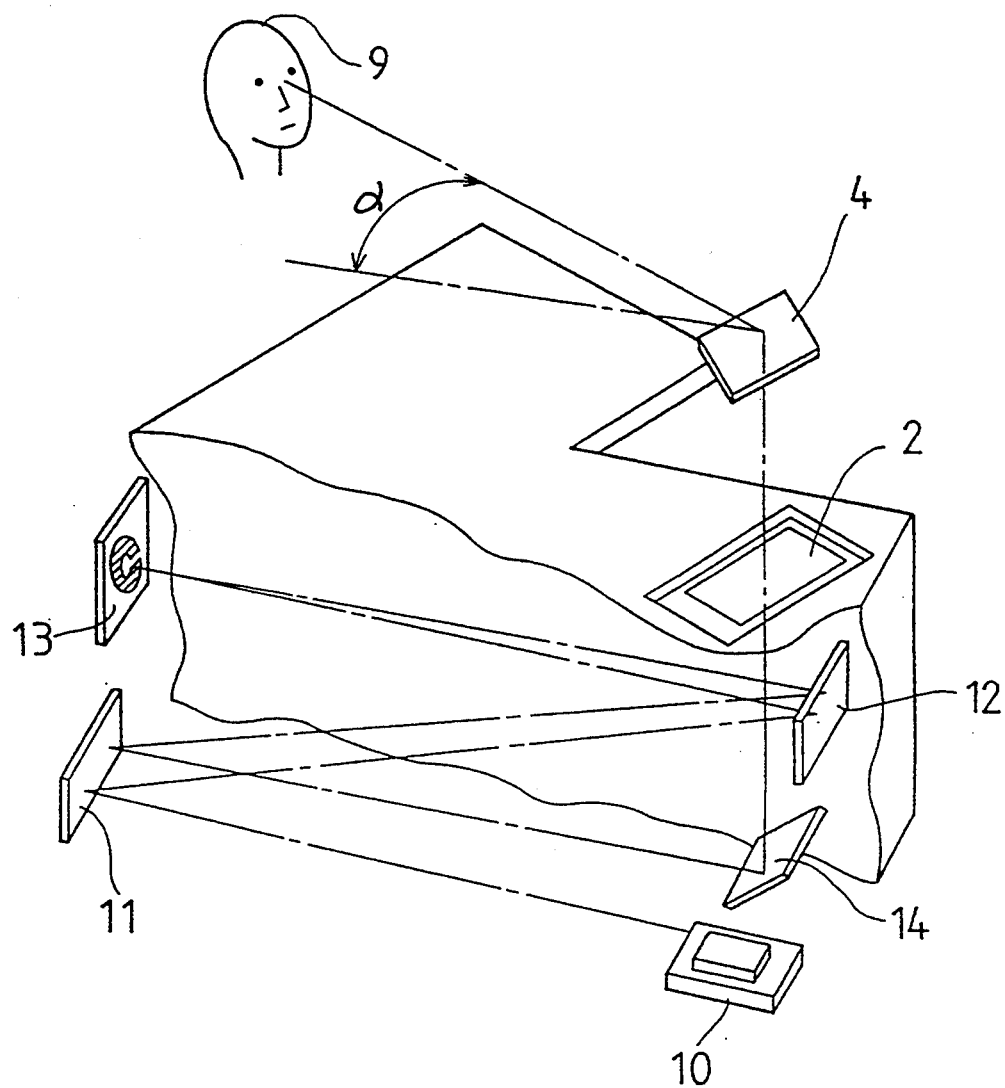
FIG. 3 is a diagrammatic view of an optical system provided in an operating table included in the optometric apparatus of FIG. 1.

Referring to FIG. 3, a test chart projector 10 constructing a vision test chart displaying device, is capable of projecting the optical images of plural of vision test marks selectively one at a time, the optical image of a vision test mark projected by the chart projector 10 is reflected in turn by a first mirror 11 and a second mirror 12 disposed in the operating table 1 on a reflective screen 13. The optical image reflected by the reflective screen 13 is reflected again through the second mirror 12 and the first mirror 11 toward a third mirror 14. The third mirror 14 deflects the optical image so as to be reflected upward through the glass window 2 on the fourth mirror 4. Then, the fourth mirror 4 reflects the optical image toward the examinee's eyes. Thus, the optical image of the vision test chart projected on the reflecting screen 13 is reflected four times by the second mirror 12, the first mirror 11, the third mirror 14 and the fourth mirror 4 in turn so that the length of the optical path of the optical image is equal to the standard far vision testing distance of 500 cm. The examinee's line of vision is inclined at an angle of α, i.e. 30° in this embodiment, to a horizontal plane including the optical path of the optical image formed by the first mirror 11, the second mirror 12 and the third mirror 14. Suitable value of the angle α is in the range of about 20° to about 45°. As a result, the optometric apparatus may require a smaller space for the visual acuity test.

FIG. 4 through FIG. 8 show several examples that a smaller space for the visual acuity test can be provided by using an optometric apparatus of the present invention As shown in FIG. 4(a), a known optometric apparatus requires a distance between the examinee and the fourth mirror 4 being not less than 100 cm. Compared with the optometric apparatus of the present invention shown in FIG. 4(b), the known optometric apparatus must provide an excessive space on the table, as indicated by oblique lines of FIG. 4(c). When disposing the optometric apparatus of FIG. 4(a) and FIG. 4(b) respectively in the corner of a room, while a large dead space as indicated by cross lines in FIG. 5(a) will be remained around the examinee, a dead space occurred by arranging the optometric apparatus of the present invention may be reduced as shown in FIG. 5(b).

Figure 8:
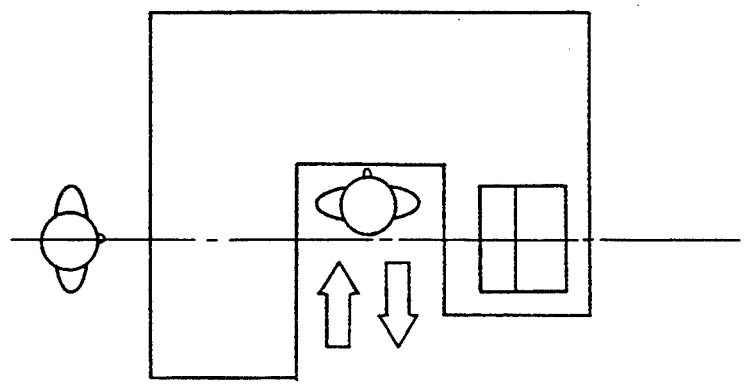
FIG. 8 is a schematic plan view showing a conventional optometric apparatus having the inconvenience when the operator will do deskwork on a table of the apparatus.

Further, by comparing the known apparatus of FIG. 6(a) and the apparatus of the present invention of FIG. 6(b), it is obvious that an adjacent part to a fourth mirror 4 on the operating table of the known apparatus formed as shown in FIG. 6(a) becomes a dead space. When the optometric apparatus of FIG. 6(a) and 6(b) are disposed in the corner of a room respectively, the examinee may go in and out more smoothly in the situation of FIG. 7(b) than of FIG. 7(a). Furthermore, the operator (examiner), when sitting in a center of an operating table of the known optometric apparatus as shown in FIG. 8, can not work efficiently on the operating table because of an existence of a table in right and left sides of the operator, further the operator can not go in and out smoothly the optometric apparatus and then must act excessively so as not to interrupt a visual field of the examinee in watching an optical image of the vision test chart. By using the optometric apparatus according to the present invention, however, such problems mentioned above may be eliminated.

Figure 9:
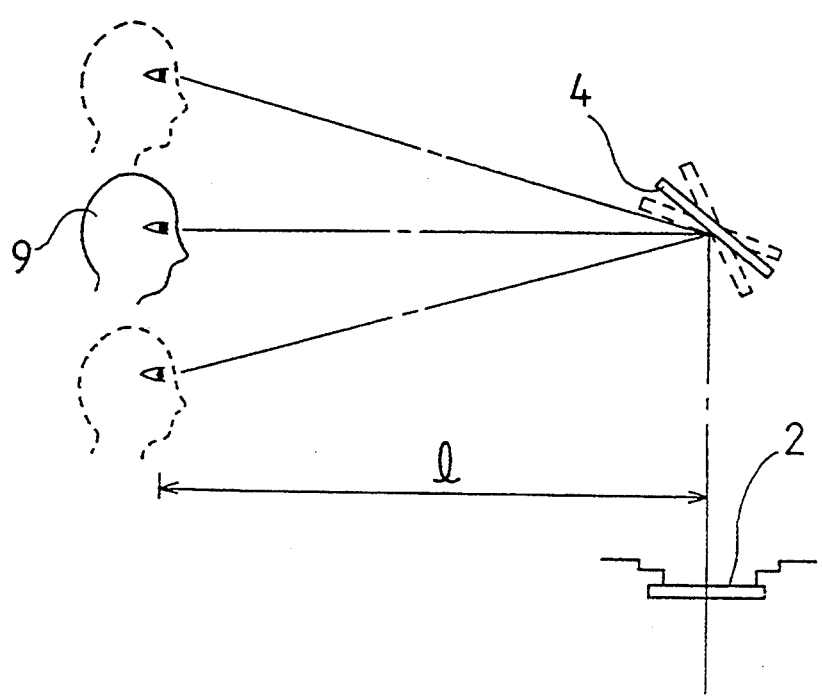
FIG. 9 is a diagrammatic view of assistance in explaining a manner of adjusting the optical path according to the height of the examinee's eye.

An optical path adjusting mechanism for adjusting the optical path according to the height of the examinee's eyes will be described hereinafter. As shown in FIG. 9, the optical path is adjusted according to the height of the examinee's eyes by changing the inclination of the fourth mirror 4. Suppose that the distance between the examinee's eyes and the fourth mirror 4 is 1000 mm. Then, if the height of the examinee's eyes is higher or lower than the standard height by 100 mm, the change of the vision testing distance from the standard vision testing distance is as small as about 5 mm, which is negligible in ordinary vision testing. The height of the examinee's eyes is detected by a subjective refractor as schematically shown in FIG. 10, and the inclination of the fourth mirror 4 is adjusted so that the examinee is able to look at the optical image of the vision test chart in the fourth mirror 4 by a control system shown in FIG. 11.

Figure 11:
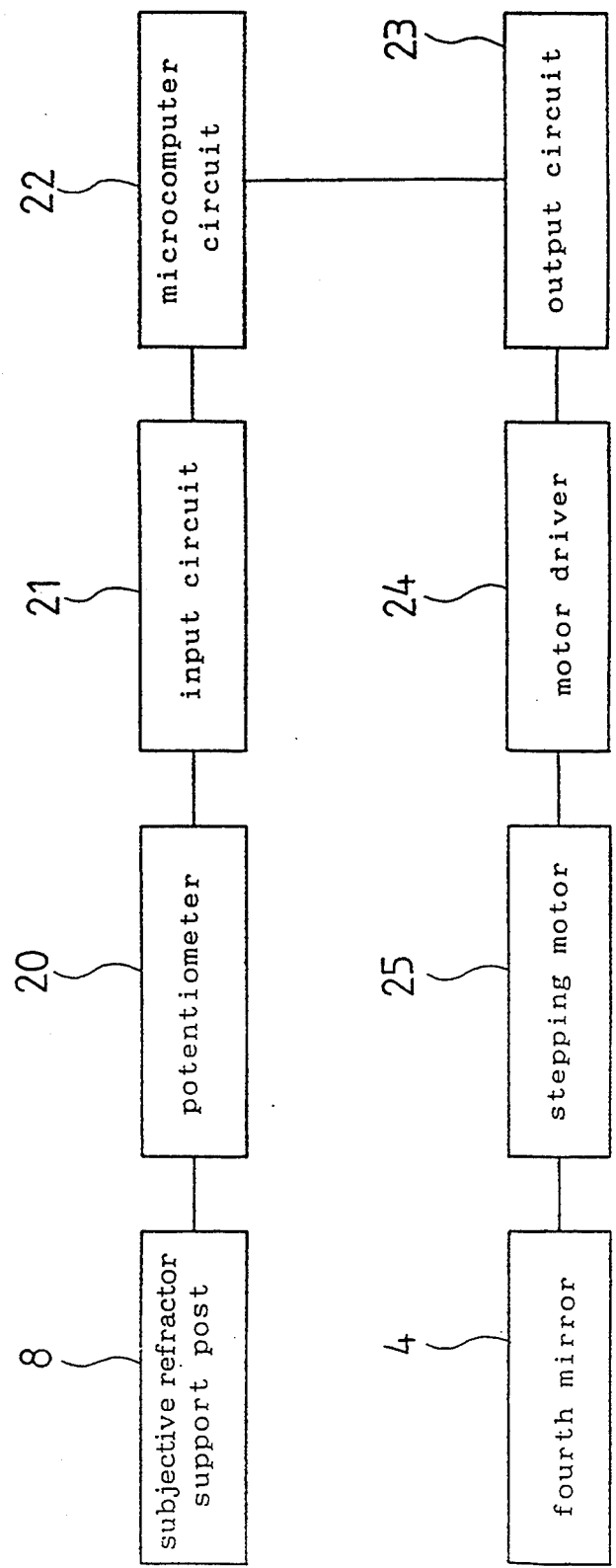
FIG. 11 is a block diagram of a control system for controlling the subjective refractor and reflecting mirrors of the optometric apparatus of FIG. 1.

Referring to FIG. 11, the length of the telescopic support post 8 is changed according to a signal provided by the controller 3 of FIG. 1 to change the height of the subjective refractor 6. The height of the subjective refractor 6 is detected by a potentiometer 20 in the telescopic support post 8 and a signal representing the height of the subjective refractor 6 is sent through an input circuit 21 to a CPU 22. Then, the CPU 22 gives a signal through an output circuit 23 to a motor driver 24 to drive a stepping motor 25 to change the inclination of the fourth mirror 4 so that the optical image is reflected by the fourth mirror 4 correctly toward the subjective refractor 6.

Figure 10:
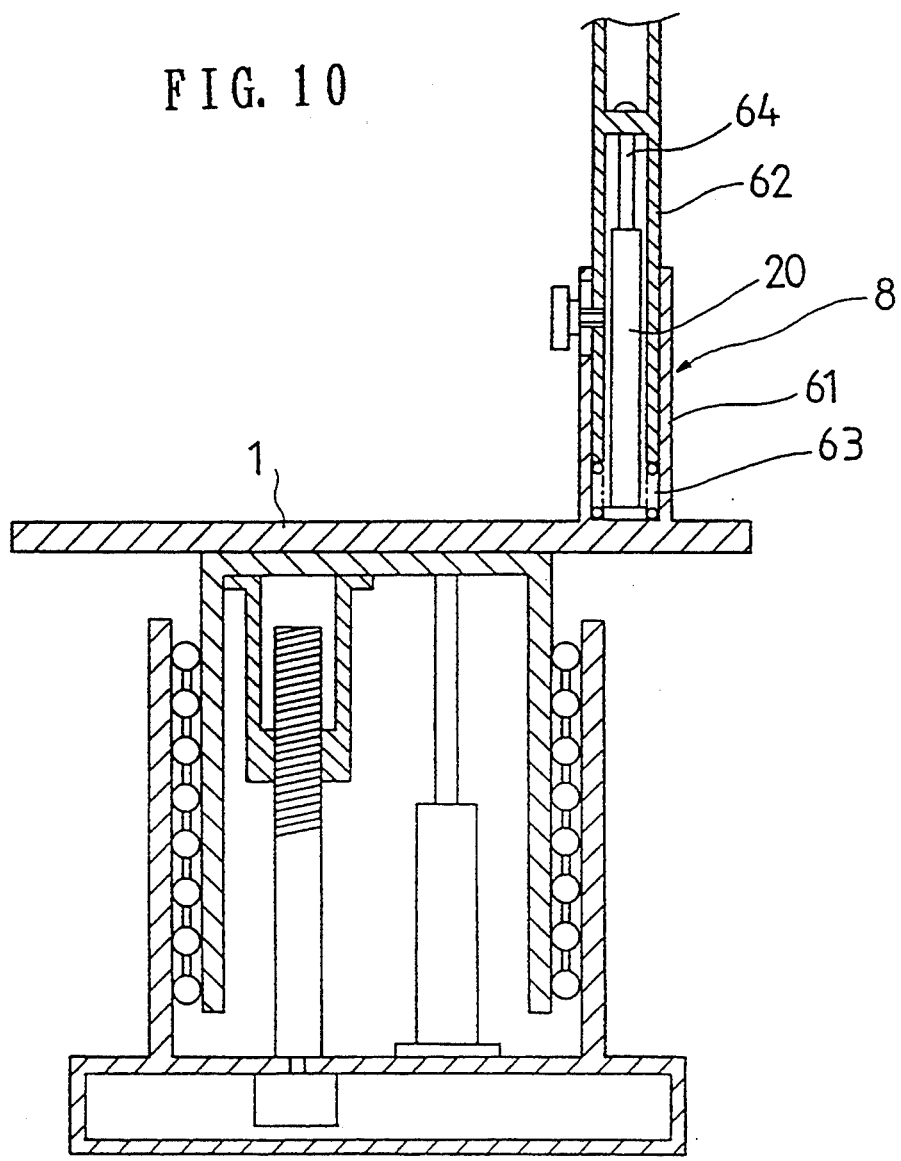
FIG. 10b is a sectional view of assistance in describing a lifting mechanism included in the optometric apparatus of FIG. 1.

Referring to FIG. 10, a support post 62 supporting the subjective refractor 6 consists of a guide pipe 81, a support post 62 inserted in the guide pipe 61, and subjecting the subjective refractor 6 thereon, and a spring 63 pushing the support post 62 up to support the subjective refractor 6 securely in place. The resistance of a potentiometer 20 attached to the table top of the operating table 1 varies according to the distance traveled by a potentiometer operating rod 64 fixed to the support post 62. The resistance of the potentiometer 20 is converted into the height of the measuring windows of the subjective refractor 6 from the upper surface of the table top of the operating table 1.

In operation, the examiner turns the subjective refractor 6 on the telescopic support post 8 to set the subjective refractor 6 in front of the examinee's eyes, operates the controller 3 to adjust the height of the subjective refractor 6. The height of the subjective refractor 6 is detected by the potentiometer 20, and the stepping motor 25 is driven according to a detection signal representing the height of the subjective refractor 6 to set the subjective refractor 6 properly in front of the examinee's eyes so that the examinee is able to look at the optical image of the vision test chart through the measuring windows of the subjective refractor 6.

The examinee's eyes are examined by changing the refractive power of the subjective refractor 6 and selectively projecting vision test marks by the test chart projector 10.

Figure 12:
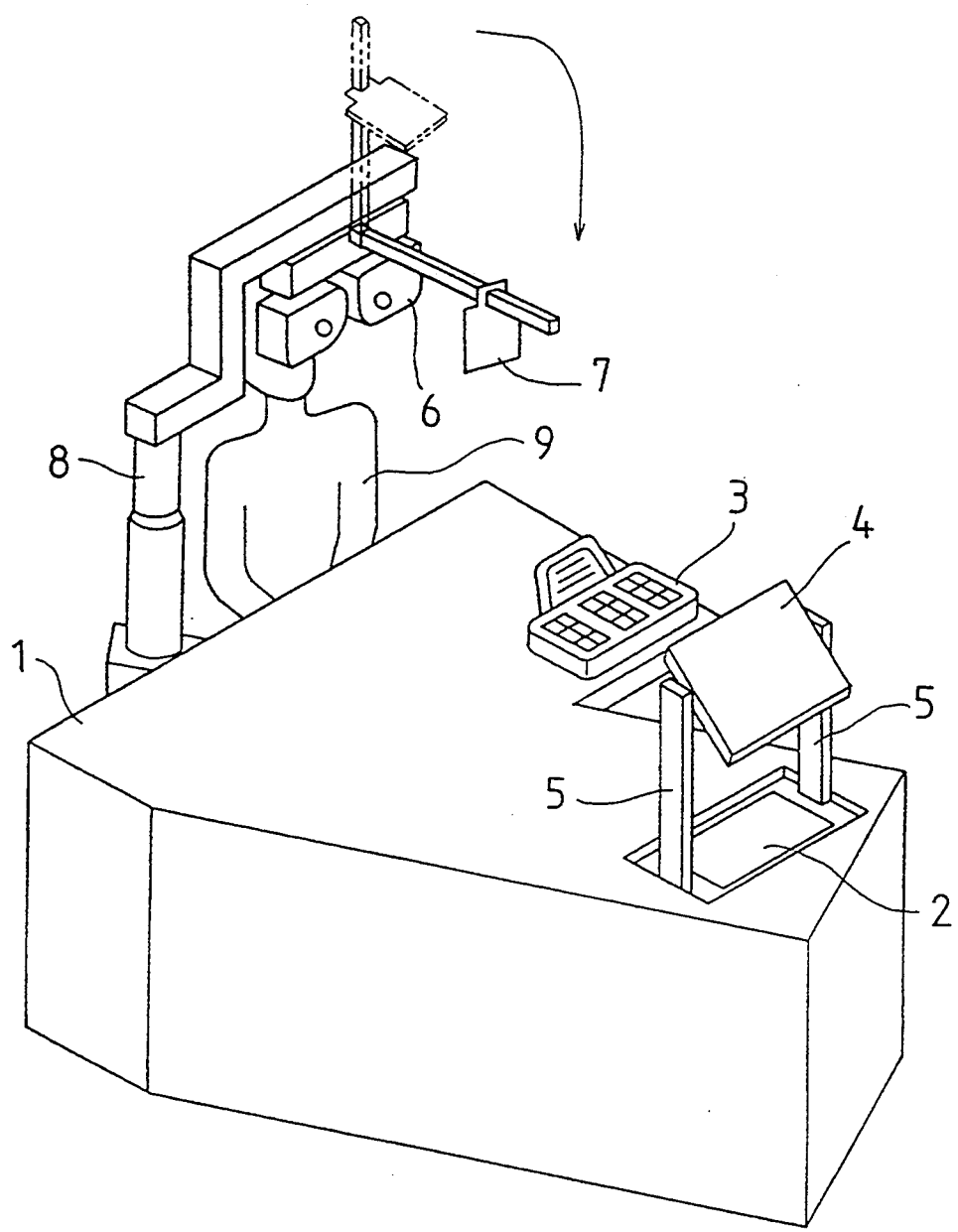
FIG. 12 is a perspective view of assistance in explaining a near vision testing procedure.

For the near vision test, the near vision test chart 7 supported on the subjective refractor 8 is turned in the direction of the arrow to set the near vision test chart 7 in front of the examinee as shown in FIG. 12.

Figure 13:
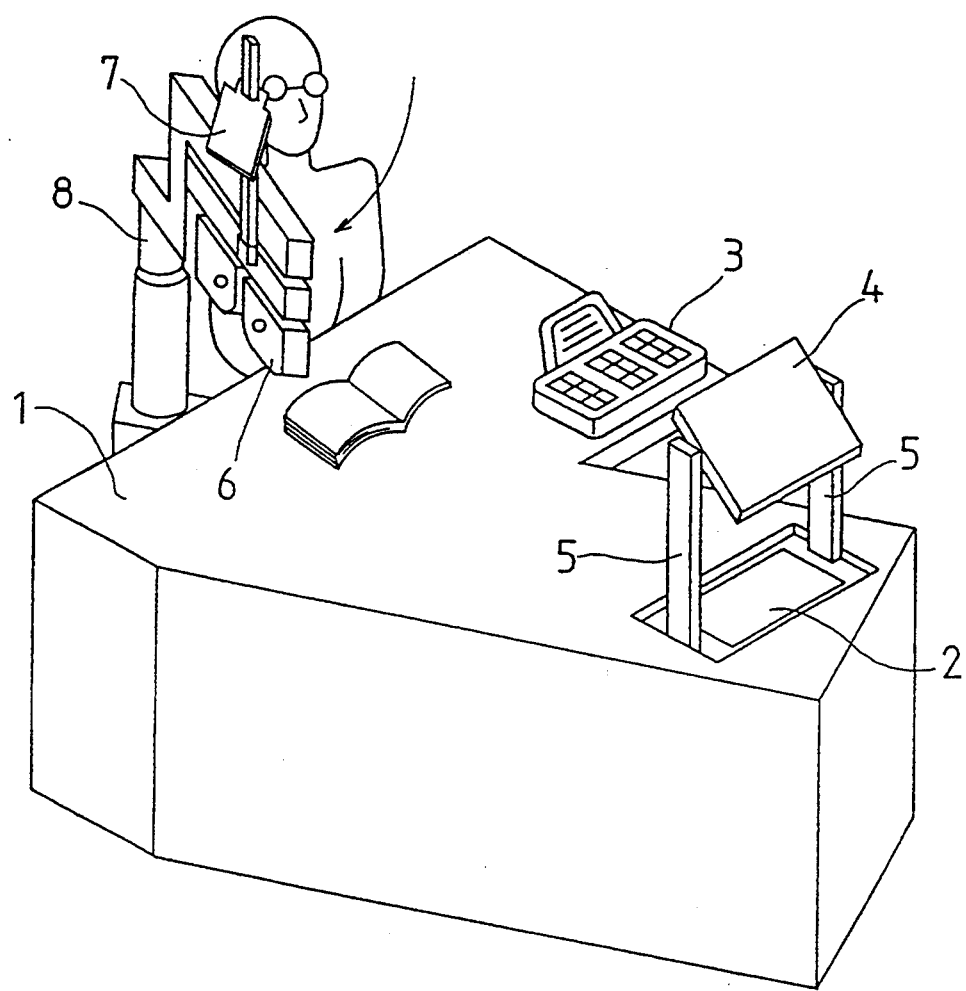
FIG. 13 is a perspective view of assistance in explaining a procedure of eye examination using a trial frame.

In testing the near vision by using a trial frame and trial lenses, the subjective refractor 8 is turned on the telescopic support post 8 to remove the same to a position on the right-hand side of the examinee as shown in FIG. 13.

Thus, a series of subjective examinations including far vision test, near vision test and the examination of the examinee's eyes can be readily achieved without removing the fourth mirror 4 for far vision test.

Various modifications of the foregoing embodiments are possible. For example, the motor-driven subjective refractor 6 shown in FIG. 1 may be substituted by a manually operated subjective refractor, and the test chart projector 10 shown in FIG. 3, may be substituted by a backlight-illuminated test chart panel. The height of the fourth mirror 4 may be changed by changing the length of a support post 5 to which the fourth mirror 4 is fixed, instead of changing the inclination of the fourth mirror 4.

Figure 14:
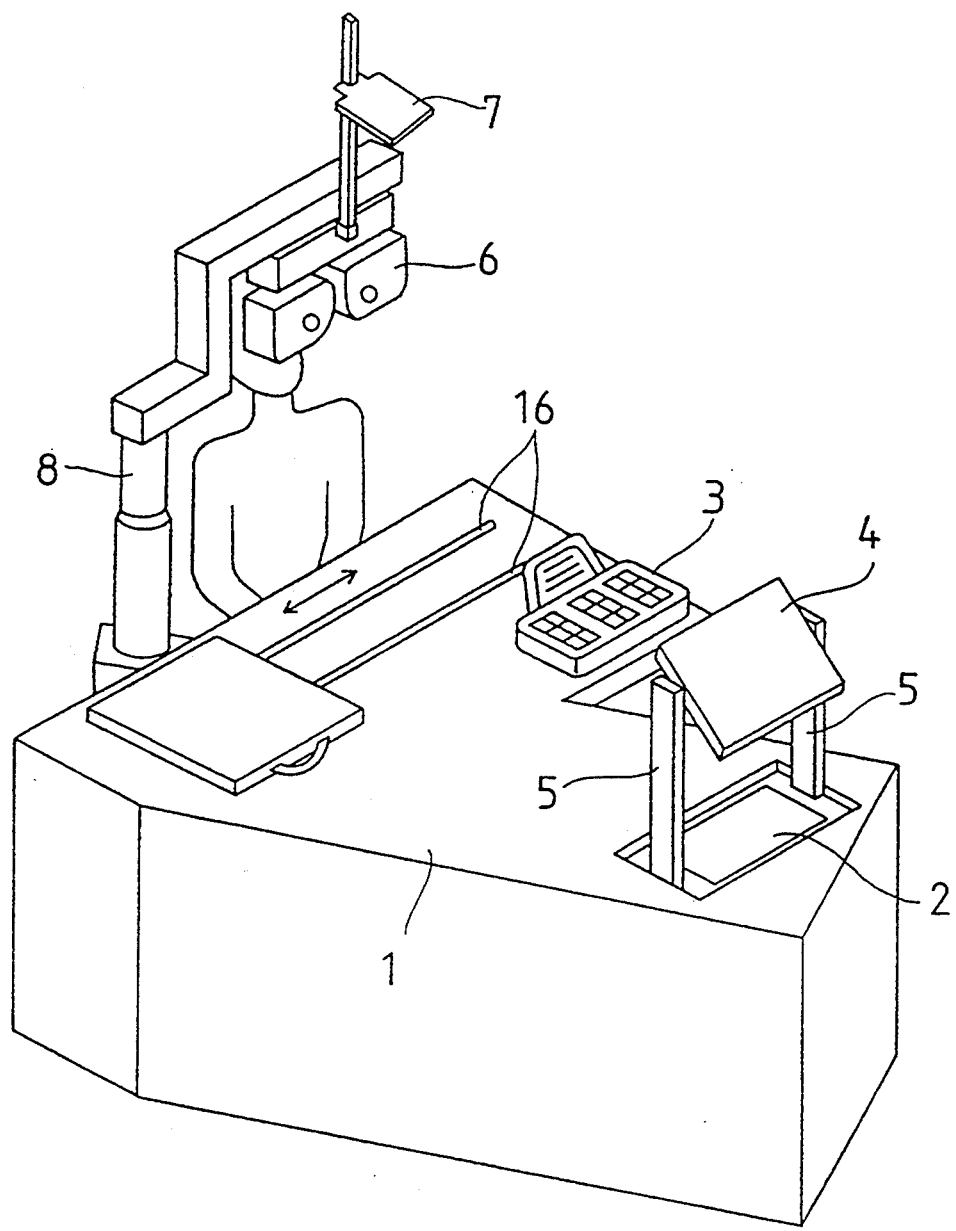
FIG. 14 is a perspective view of a modification of the optometric apparatus of FIG. 1, incorporating improvements.

Furthermore, as shown in FIG. 14, the operating table 1 may be provided with guide rails 18 on the upper surface thereof, a carriage placed on the operating table 1 for movement along the guide rails 16, and an objective refractor 8 or the like mounted on a carriage, for the additional examination of the examinee's eyes.

Figure 15:
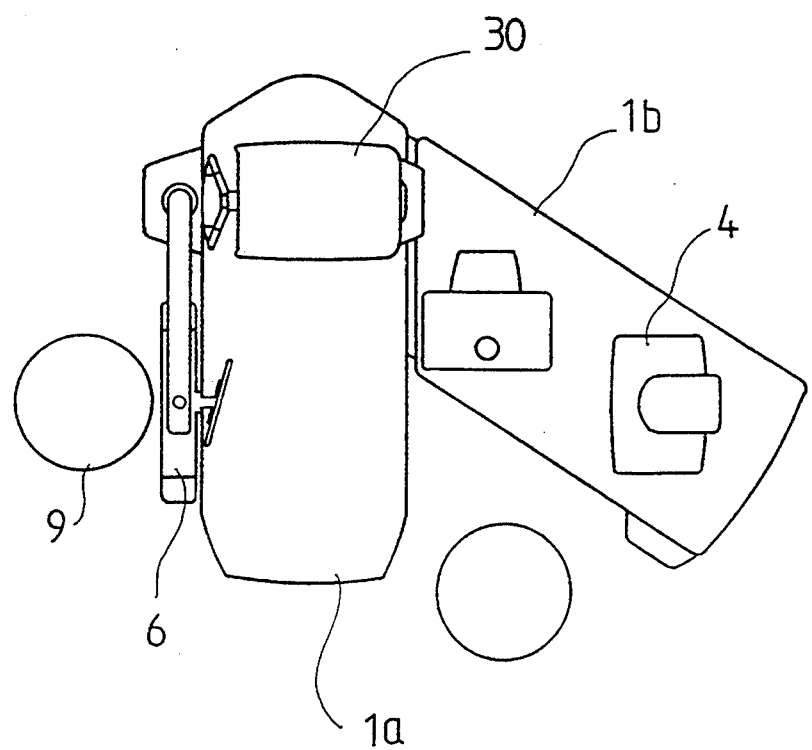
FIG. 15 is a schematic plan view of an optometric apparatus embodying another embodiment according to the present invention.
Figure 16:
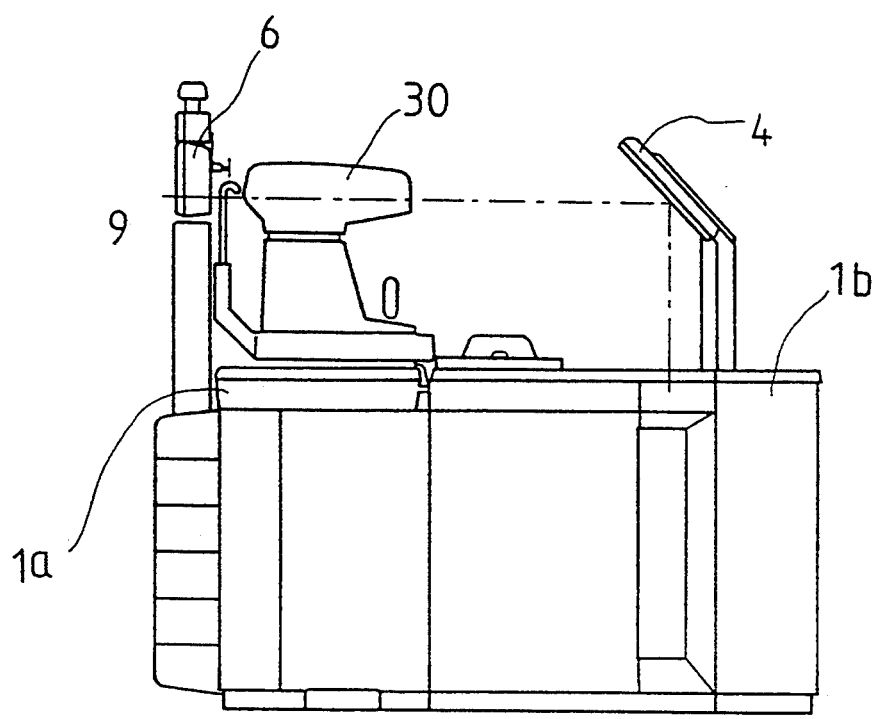
FIG. 16 is a schematic front view of an optometric apparatus of FIG. 15.
Figure 18:
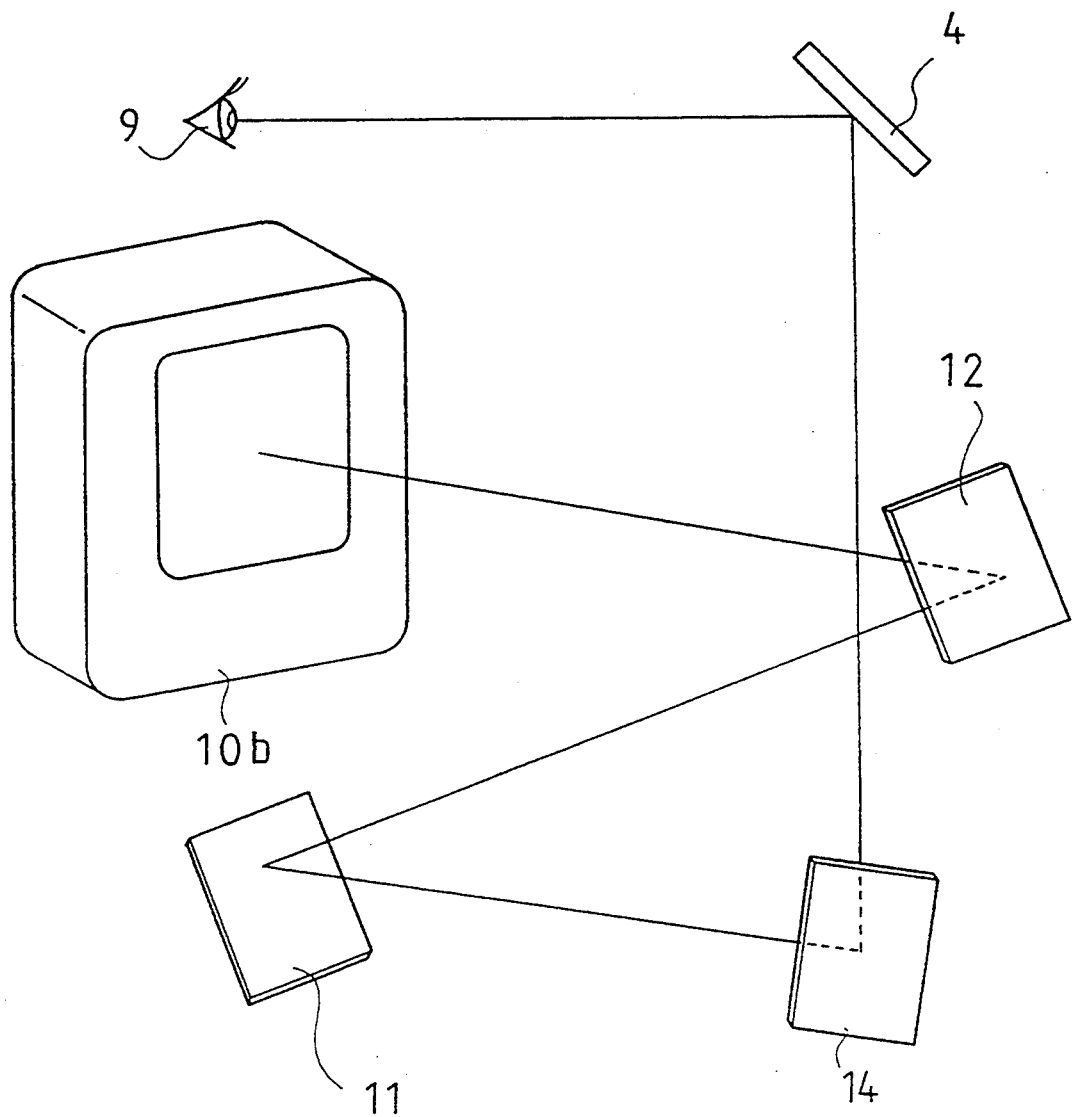
FIG. 18 is a perspective view of explaining a test chart displaying apparatus of backlight-illuminated type.

FIG. 15 and FIG. 16 show an optometric apparatus in the second embodiment according to the present invention, specifically, FIG. 15 shows a plane view of the optometric apparatus, and FIG. 18 shows a front view of FIG. 15.

Figure 17:
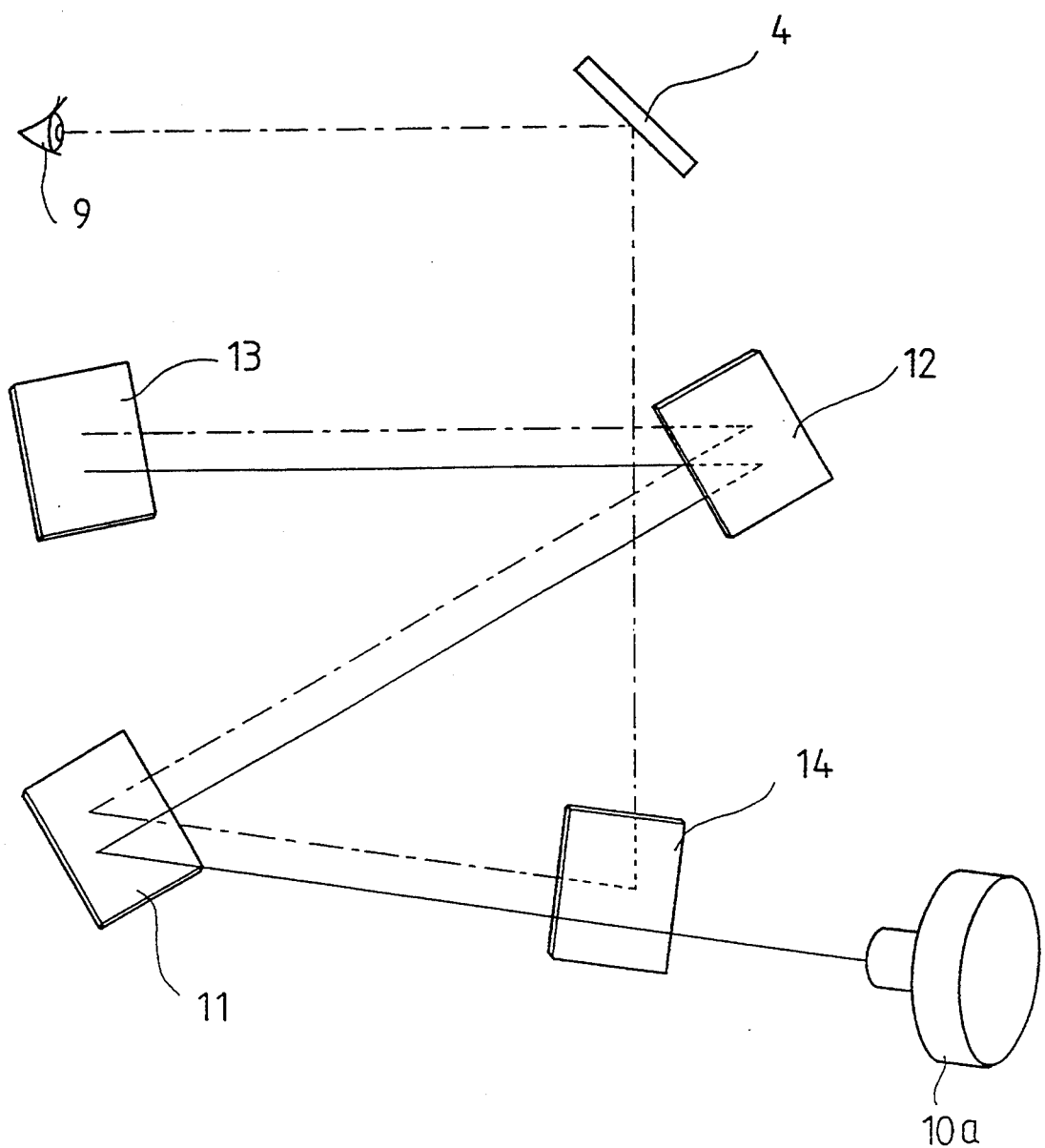
FIG. 17 is a schematic diagram of explaining the optical system contained in an operating table.

Referring to these FIGS. 15 and 16, in the optometric apparatus, an operating table 1a on which a subjective refractor 6 and an objective refractor 30 are mounted, in which the operating table 1a is provided separately from a vision test chart displaying table 1b. As shown in FIG. 17, the vision test chart displaying table 1b is provided internally with a vision test chart projector 10a as a vision test chart projecting device for projecting an image of a vision test chart through a first reflecting mirror 11 and a second reflecting mirror 12 onto a reflecting screen 13. In order that the examinee may look at the optical image in a form of an erecting image on a fourth mirror 4, the reflecting screen 13 and the vision test chart are inclined at an angle adjusted according to the twist of an incident surface of a third mirror 14 and that of a fourth mirror 4 respectively to a plane including the optical paths of the optical image formed by the first mirror 11 and the second mirror 12, so that the examinee is able to look at an optical image in a form of an erecting image on a fourth mirror 4.

The optical image of the vision test chart projected on the reflecting screen 13 travels repeatedly through reflecting mirrors 12, 11, 14 and a last mirror 4 toward the examinee's eyes 9 so that the examinee can watch the optical image of the vision test chart. It will be understood that a backlight-illuminated test chart projector 10b as shown in FIG. 18 can be used as a vision test chart projecting device.

A vision test chart projector 10a includes a polarizing vision test chart utilizing a polarized light character to measure various function including each visual acuity of right and left eyes and the like respectively with the eyes opening.

Figure 19:
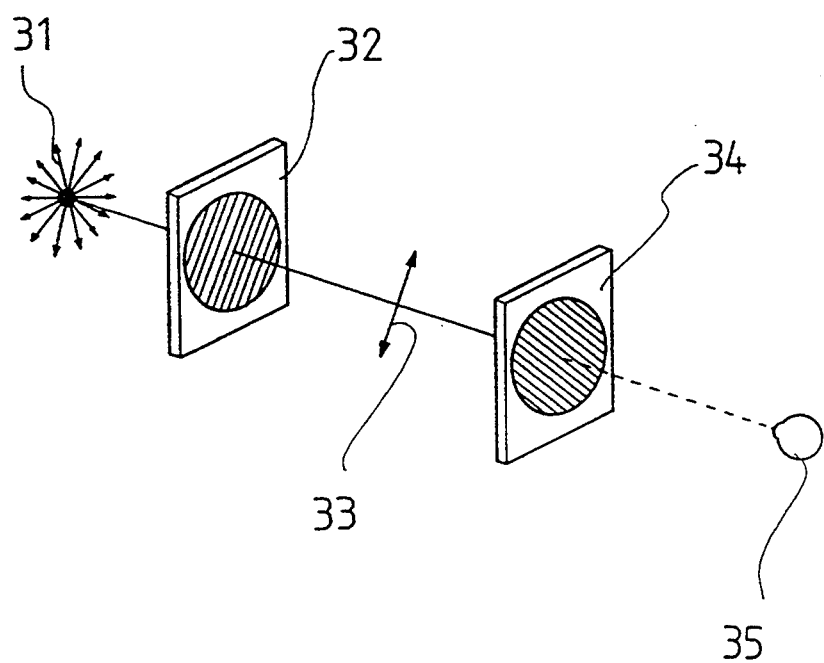
FIG. 19 is a schematic diagram of explaining the principle of the function of polarizing plate.

A functional test of the eyes with binocular vision using the polarized light character is generally explained as follows, referring to FIG. 19. The natural light beam transmitted through a polarizing plate 32, while is permitted transmitting through a polarizing plate having a same polarizing axis as that of the polarizing plate 32, is not permitted transmitting through a polarizing plate 34 having a vertical polarizing axis to that of the polarizing plate 32, whereby the light beam can not travel to observer's eyes 35.

Figure 20:
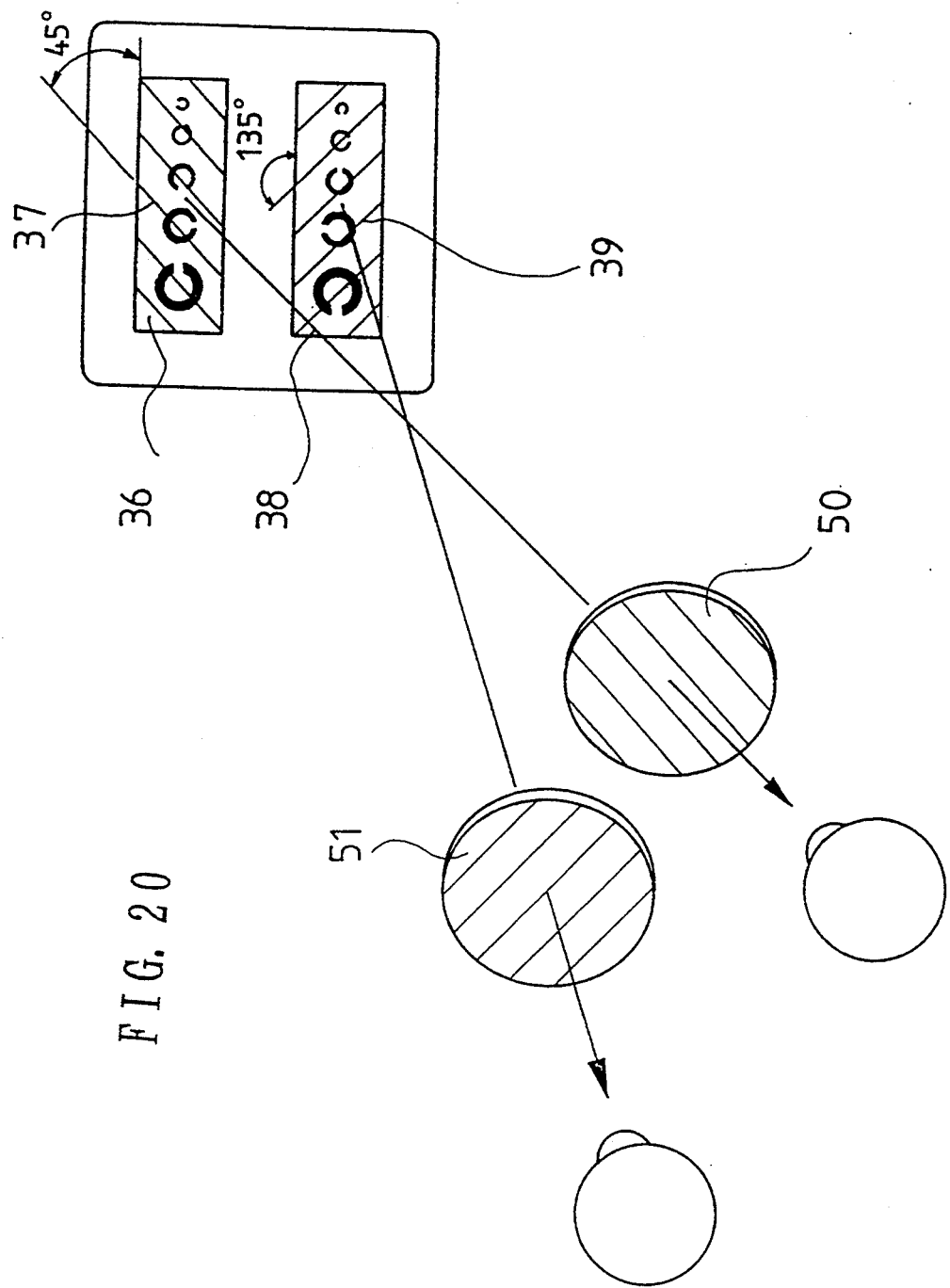
FIG. 20 is a perspective view of explaining a standard vision acuity test using polarizing plates.

FIG. 20 shows schematically a standard test example using such vision test chart mentioned above to measure each visual acuity of right and left eyes with binocular vision. In the vision test chart, there are an upper Landolt ring vision test chart 36 having a polarizing axis 37 inclined at an angle of 45° to a horizontal direction and a lower Landolt ring vision test chart 38 having a polarizing axis 39 inclined to a vertical direction to the polarizing axis 37, that is, at an angle of 135° to a horizontal direction. The subjective refractor (or trial glasses) disposed in a front of the examinee's eyes is provided internally with a polarizing plate 50 for right eye and a polarizing plate 51 for left eye. The polarizing plate 50 has a polarizing axis inclined at the same angle as the polarizing axis 37 of the Landolt ring vision test chart 36, similarly the polarizing plate 51 has a polarizing axis inclined to the same direction as the polarizing axis 39. Thus, because of a polarizing character, visual acuity test of right and left eyes may be achieved with both eyes opening.

In the present invention, there is a distinguished character in a method to determine a polarizing axis direction of a polarizing plate in a subjective refractor and that of a polarized vision test chart, as described below.

It is understood that a polarizing light character may be changed through mirror reflection in an apparatus utilizing reflecting mirrors such as the present invention. The reason is as follows.

Generally, as a kind of polarized light, there are linearly polarized light, of which the end of amplitude is always in a plane including a progressive direction, e.g. a polarized light 33 in FIG. 21, circularly polarized light of which the end of amplitude moves in a circle within a vertical plane to a propagation direction, and elliptically polarized light which that of amplitude thereof moves in an ellipse. Even if reflected by plural mirrors, when the light beam is incident into each surface of the mirrors in an approximate same incident plane, there will not occur any problem because the form of elliptically polarized light is close to a linearly polarized light. When a plane of incidence of a mirror is disposed at a twisted position with respect to that of another mirror, the linearly polarized light beam incident into a reflecting mirror will become elliptically polarized light beam toward another mirror by a reflecting mirror.

Figure 22:
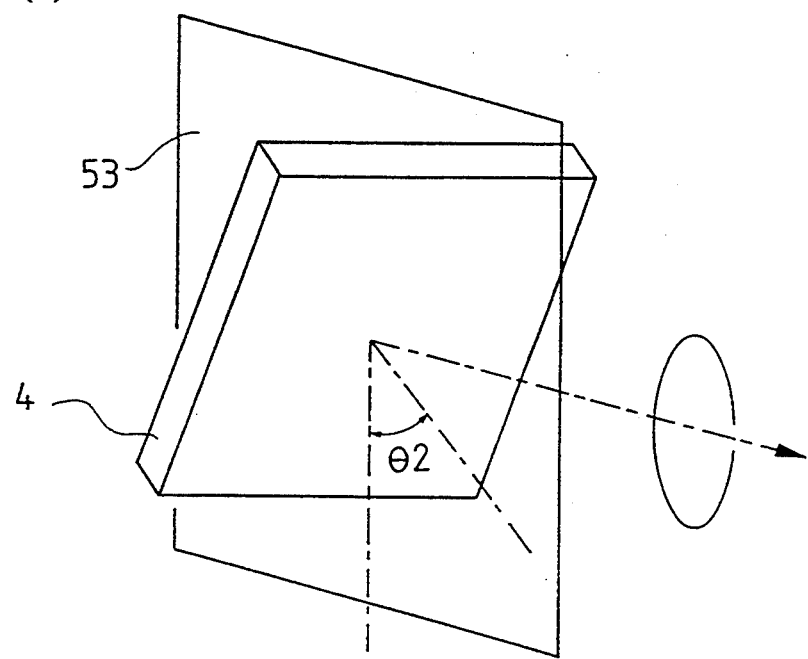
FIG. 22 is a perspective schematic view of explaining a method of determining an angle of polarizing axis.
Figure 22:
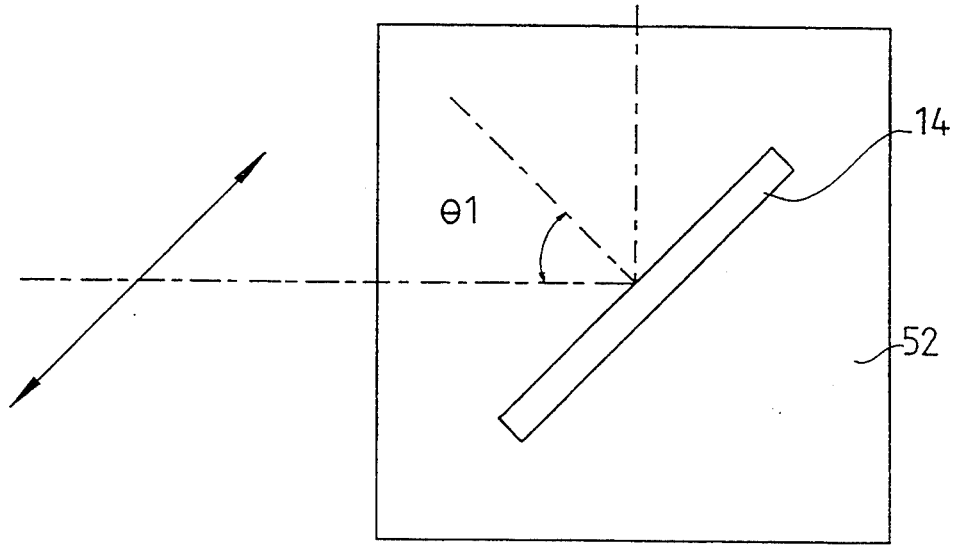

As shown in FIG. 22, when an incident plane 52 of a reflecting mirror 14 and an incident plane 53 of a reflecting mirror 4 are not on the same plane, the elliptically polarized light will move in a form of an approximate circle polarized light according to the extent of the twist between these incident planes 52, 53. Thus, the optical image of the vision test chart can not disappear through a polarizing plate of a subjective refractor disposed in a front of the examinee's eyes.

However, the light to be projected toward the examinee may become a linearly polarized light by setting each angle of polarizing axis of vision test charts separately (standard angle are 45° and 135° respectively). Therefore, when the angle of a polarizing axis of each polarizing plate is adjusted according to that of each vision test chart, the optical image of the vision test chart through a polarizing plate having a different axis angle from the vision test chart of the subjective refractor may be disappeared.

More particularly, a polarizing axis angle will be determined as follows, referring to FIG. 22 showing a pair of mirrors 14 and 4 formed of aluminium. Reflecting linearly polarized light beam by a first mirror 14 changes the character of polarized light. In classifying the linearly polarized light into a vibrational wave progressing to a vertical direction with respect to an incident plane (S-polarized light) and another vibrational wave progressing to a paralle direction (P-polarized light), the reflectance of a reflective surface of a first mirror Rs1, Rp1 are given by the formula (1) and (2).

$$R_{S1} = \frac{(a_1 - a_2)^2 + (b_1 - b_2)^2}{(a_1 + a_2)^2 + (b_1 + b_2)^2} \quad (1)$$

$$R_{P1} = R_{S1} \cdot \frac{(a_1 a_2 - b_1 b_2 - c^2)^2 + (a_1 b_2 + a_2 b_1)^2}{(a_1 a_2 - b_1 b_2 + c^2)^2 + (a_1 b_2 + a_2 b_1)^2} \quad (2)$$

where a refractive index of the air is $n_1$, a refractive index of aluminium mirror is $n_2$, an absorption coefficient of aluminium mirror is $k_2$, and an incident angle of the polarized light to first mirror is $\theta_1$, the following formula (3) is obtained.

$$a_1 = n_1 \cos\theta_1 \quad (3)$$

$$b_1 = 0$$

$$c = n_1 \sin\theta_1$$

$$2a_2^2 = \{(n_2^2 + k_2^2)^2 - 2n_1^2 \sin^2\theta_1(n_2^2 - k_2^2) + n_1^4 \sin^4\theta_1\}^{\frac{1}{2}} +$$
$$(n_2^2 - k_2^2 - n_1^2 \sin^2\theta_1)$$

$$2b_2^2 = \{(n_2^2 + k_2^2)^2 - 2n_1^2 \sin^2\theta_1(n_2^2 - k_2^2) + n_1^4 \sin^4\theta_1\}^{\frac{1}{2}} -$$
$$(n_2^2 - k_2^2 - n_1^2 \sin^2\theta_1)$$

A phase angle difference ($\Delta\phi_1$) between S and P polarized light occurred after reflecting by a reflecting mirror is found based on a formula (4).

$$\Delta\phi_1 = \quad (4)$$

$$\cos^{-1}\left\{ \frac{\sqrt{R_{S1}}}{\sqrt{R_{P1}}} \cdot \frac{(a_1^2 + b_1^2)(a_2^2 + b_2^2) - c^4}{(a_1 a_2 - b_1 b_2 + c^2)^2 + (a_1 b_2 + a_2 b_1)^2} \right\}$$

Considering a linearly polarized light having a polarizing plane which is inclined at an angle of $\alpha_1°$ to an incident plane of a first mirror, and an incident light are decomposed into S and P elements according to formula (5), an amplitude of a polarized light is $E_0$.

$$E_{PO} = E_o \cos\alpha_1$$

$$E_{SO} = E_0 \, l \sin\alpha_1 \quad (5)$$

When S and P elements of amplitude of a reflected light beam are $E_{S1}$, $E_{P1}$ respectively, these $E_{S1}$, $E_{P1}$ are found by the formula (6).

$$E_{P1} = E_{PO} \sqrt{R_{P1}} \quad (6)$$

$$E_{S1} = E_{SO} \sqrt{R_{S1}}$$

Further, when an incident plane of a second mirror is inclined at an angle of $\delta$ against the incident plane of a first mirror, a first reflected light with respect to a second incident plane is decomposed as follows into S and P elements.

$$E_{P2} = \sqrt{\frac{4B'}{4A'B' - C^2}} \quad (7)$$

$$E_{S2} = \sqrt{\frac{4A'}{4A'B' - C^2}}$$

$$\Delta\phi_2 = \cos^{-1}\left(-\frac{C}{2\sqrt{A'B'}}\right)$$

where the formula (8), $$A' = A\cos^2\delta + B\sin^2\delta - C\sin\delta\cos\delta \quad (8)$$

$$B' = A\sin^2\delta + B\cos^2\delta + C\sin\delta\cos\delta$$

$$C' = (A - B)\sin 2\delta + C\cos 2\delta$$

$$A = \frac{1}{(E_{P1}\sin\Delta\phi_1)^2}$$

$$B = \frac{1}{(E_{S1}\sin\Delta\phi_1)^2}$$

$$C = \frac{-2\cos\Delta\phi_1}{E_{P1}E_{S1}\sin^2\Delta\phi_1}$$

In a reflective character of the second mirror, the refractivity $R_{S2}$, $R_{P2}$ are found according to formula (9). Further, $$R_{S2} = \frac{(d_1 - d_2)^2 + (e_1 - e_2)^2}{(d_1 + d_2)^2 + (e_1 + e_2)^2} \tag{9}$$

$$R_{P2} = R_{S2} \cdot \frac{(d_1 d_2 - e_1 e_2 - f^2)^2 + (d_1 e_2 + d_2 e_1)^2}{(d_1 d_2 - e_1 e_2 + f^2)^2 + (d_1 e_2 + d_2 e_1)^2}$$

When an incident angle to the second mirror 4 is $\phi 2$, $$d_1 = n_1 \cos\theta_2 \tag{10}$$

$$e_1 = 0$$

$$f = n_1 \sin\theta_2$$

$$2d_2^2 = \{(n_2^2 + k_2^2)^2 - 2n_1^2 \sin\theta_2^2(n_2^2 - k_2^2) + n_1^4 \sin^4\theta_2\}^{\frac{1}{2}} +$$
$$(n_2^2 - k_2^2 - n_1^2 \sin^2\theta_2)$$

$$2e_2^2 = \{(n_2^2 + k_2^2)^2 - 2n_1^2 \sin\theta_2^2(n_2^2 - k_2^2) + n_1^4 \sin^4\theta_2\}^{\frac{1}{2}} -$$
$$(n_2^2 - k_2^2 - n_1^2 \sin^2\theta_2)$$

$$e_1 = 0$$

Then, the phase angle difference ($\Delta\phi_3$) between S and P polarized light is found as follows.

$$\Delta\phi_3 = \cos^{-1}\left\{ \frac{\sqrt{R_{S1}}}{\sqrt{R_{P1}}} \cdot \frac{(d_1^2 + e_1^2)(d_2^2 + e_2^2) - f^4}{(d_1 d_2 - e_1 e_2 + f^2)^2 + (d_1 e_2 + d_2 e_1)^2} \right\} \tag{11}$$

where S and P elements of amplitude of reflected light by the second mirror are Es3, Ep3 respectively, $$E_{P3} = E_{P2} \sqrt{R_{P2}} \tag{12}$$

$$E_{S3} = E_{S2} \sqrt{R_{S2}}$$

The final phase angle difference ($\Delta\phi_4$) may be obtained according to the formula (13).

$$\Delta\phi_4 = \Delta\phi_2 + \Delta\phi_3 \tag{13}$$

It is understood that the reflected light beam by the second mirror may become a linearly polarized light, provided $\Delta\phi_4$ equales to 0,180 degree. The incident angle $\alpha_1$ to obtain such value can be found according to above formulas. If the optical image is reflected repeatedly by plural mirrors, the above formulas will be repeated again.

Based on the value of $\alpha_1$, the polarizing axis angle of a vision test chart displaying device may be determined.

Furthermore, an angle $\alpha_2$ between a polarized plane of a final reflected light and an incident plane of the second mirror which has become a linearly polarized light will be given in the formula (14), so that the polarizing axis angle of a polarizing plate of the subjective refractor disposed in a front of the examinee may be determined according to the above angle $\alpha_2$.

$$\alpha_2 = \tan^{-1} \frac{E_{S3}}{E_{P3}} \tag{14}$$

For example, when $n_1=1$, $n_2=0.76$, $k_2=5.32$, $\theta_1=\theta_2=45°$, $\delta=-32.5°$, the polarized light angle are found as follows, $$\alpha_1 = 73°, -17°, \alpha_2 = 105°, 15°$$

As described above, it is possible to find a polarized axis angle of a vision test chart displaying device and an axis angle of a polarizing plate of a subjective refractor. Preferably, a value confirmed by the experiments may be used to avoid an error in refractive constant of a surface of aluminium mirror and an effect by another plural mirrors.

Figure 23:
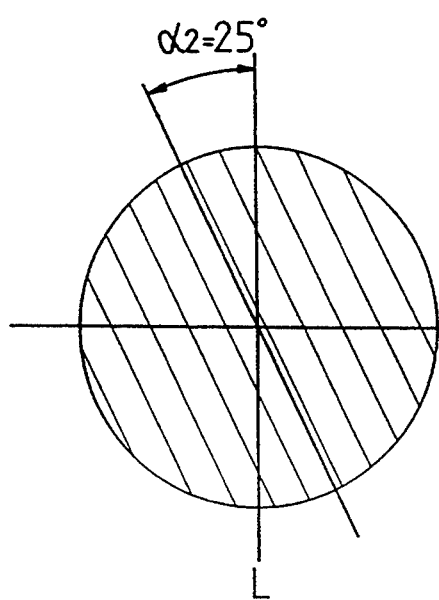
FIG. 23 is a schematic diagram of explaining an angle of a polarizing axis of polarizing plate in the second embodiment of the present invention.
Figure 23:
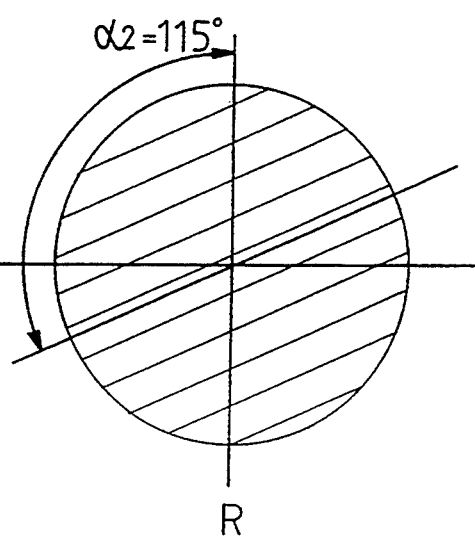

In the above embodiment, an incident plane of fourth mirror 4 is twisted at an angle of 32.5° with respect to an incident plane of third mirror 14 as shown in FIG. 17. If a linearly polarized light, then is confirmed experimentally, when a polarized light axis are $-7.5°$, $82.5°$ respectively with respect to an incident plane of the first mirror, the polarized light becomes a linearly polarized light after reflected by the second mirror. As shown in FIG. 23, the polarized axis angle of a polarizing plate of the subjective refractor are found, as 25°, 115° respectively with respect to an incident plane of the second mirror.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An optometric apparatus comprising:
    an operating table including a first table extending in right and left directions with respect to an examinee and a second table intersecting the first table at an angle, the intersecting angle between the first and second tables being an acute angle;
    a vision test chart displaying device provided internally within said operating table;
    an optical group, including a plurality of reflection-type optical elements, disposed within said operating table, wherein the optical group repeatedly reflects an optical image of the vision test chart provided from said vision test chart displaying device within said operating table, and wherein an optical path of the optical group is retained within the second table in a longitudinal direction thereof, along which the optical image is delivered;
    a first deflecting optical element for reflecting the optical image of the vision test chart reflected by said reflection-type optical elements of the optical group outside said operating table in a first direction;
    a second deflecting optical element for reflecting the optical image of the vision test chart reflected by said first deflecting optical element in a second direction toward the examinee's eyes;
    whereby a line of vision of the examinee in looking at the optical image reflected by the second deflecting optical element obliquely intersects a plane passing through the optical path defined by the optical group; and wherein said second deflecting optical element is disposed in a position not less than 70 cm from the examinee's eyes.

2. An optometric apparatus comprising:

an operating table which comprises a first table extending in right and left directions with respect to an examinee and a second table intersecting the first table at an angle, the intersecting angle between the first and second tables being an acute angle;

a vision test chart displaying device provided internally within said operating table;

an optical group, including a plurality of reflection-type optical elements, disposed within said operating table, wherein the optical group repeatedly reflects an optical image of the vision test chart provided from said vision test chart displaying device within said operating table, and wherein an optical path of the optical group is retained within the second table in a longitudinal direction thereof, along which the optical image is delivered;

a first deflecting optical element for reflecting the optical image of the vision test chart reflected by said reflection-type optical element groups outside said operating table in a first direction;

a second deflecting optical element for reflecting the optical image of the vision test chart reflected by said first deflecting optical element in a second direction toward the examinee's eyes; and turning means for turning said second deflecting optical element to adjust the reflection of the optical image to the height of the examinee's eye, wherein the turning means includes a control unit to finely control the turning angle of the second deflecting optical element in accordance with an actuating signal;

wherein a line of vision of the examinee in looking at the optical image reflected by the second deflecting optical element obliquely intersects a plane passing through the optical path defined by the optical group; and wherein said second deflecting optical element is disposed in a position not less than 70 cm from the examinee's eye.

3. An optometric apparatus comprising:

an operating table;

a vision test chart displaying device provided internally within said operating table;

an optical group, including a plurality of reflection-type optical elements, disposed within said operating table, wherein the optical group repeatedly reflects an optical image of the vision test chart provided from said vision test chart displaying device along an optical path within said operating table;

a first deflecting optical element for reflecting the optical image of the vision test charge reflected by said reflection-type optical element group outside said operating table in a first direction;

a second deflecting optical element for reflecting the optical image of the vision test chart reflected by said first deflecting optical element in a second direction toward the examinee's eyes;

turning means for turning said second deflecting optical element to adjust the reflection of the optical image to the height of the examinee's eye;

a height detecting means for detecting a height of the examinee's eye; and mirror turning angle control means for controlling a turning angle of said second deflecting optical element based on the signal detected by said height detecting means;

wherein a line of vision of the examinee in looking at the optical image reflected by the second deflecting optical element obliquely intersects a plane passing through the optical path defined by the optical group.

4. An optometric apparatus according to claim 3, further comprising a subjective refractor capable of being moved insertably to a position close to and in the line of vision of the examinee's eyes, and wherein said height detecting means for detecting the height of the examinee's eyes comprises a detecting means for detecting the height of said subjective refractor as a substitute means for detecting the height of the examinee's eyes.

5. An optometric apparatus comprising:

an operating table;

a vision test chart displaying device provided internally within said operating table;

an optical group, including a plurality of reflection-type optical elements, disposed within said operating table, wherein the optical group repeatedly reflects an optical image of the vision test chart provided from said vision test chart displaying device along an optical path within said operating table;

a first deflecting optical element for reflecting the optical image of the vision test chart reflected by said reflection-type optical element group outside said operating table in a first direction;

a second deflecting optical element for reflecting the optical image of the vision test chart reflected by said first deflecting optical element in a second direction toward the examinee's eyes; and turning means for turning said second deflecting optical element to adjust the reflection of the optical image to the height of the examinee's eye;.

wherein a line of vision of the examinee in looking at the optical image reflected by the second deflecting optical element obliquely intersects a plane passing through the optical path defined by the optical group; and wherein said second deflecting optical element is disposed in a position not less than 70 cm from the examinee's eyes.

6. An optometric apparatus according to claim 1, wherein said test chart displaying device comprises a chart projector capable of protecting plural vision test charts selectively.

7. An optometric apparatus according to claim 5, wherein said vision test chart displaying device includes a backlight-illuminated test chart.

8. An optometric apparatus comprising:

an operating table;

a vision test chart displaying device provided internally within said operating table;

an optical group, including a plurality of reflection-type optical elements, disposed within said operating table, wherein the optical group repeatedly reflects an optical image of the vision test chart provided from said vision test chart displaying device along an optical path within said operating table;

a first deflecting optical element for reflecting the optical image of the vision test chart reflected by said reflection-type optical element groups outside said operating table in a first direction;

a second deflecting optical element for reflecting the optical image of the vision test chart reflected by said first deflecting optical element in a second direction toward the examinee's eyes;

wherein a line of vision of the examinee in looking at the optical image reflected by the second deflecting optical element obliquely intersects a plane passing through the optical path defined by the optical group; and wherein said vision test chart displaying device comprises:

a right eye polarizing light vision test chart and a left eye polarizing light vision test chart, wherein a polarizing light axis of the right eye polarizing light vision test chart intersects a polarizing light axis of the left eye polarizing light vision test chart;

a right eye polarizing plate and a left eye polarizing plate, wherein a polarizing axis of the right eye polarizing plate intersects with a polarizing axis of the left eye polarizing plate;

wherein an angle of the polarizing light axis of at least one of the right and left eye polarizing light vision test charts is determined based on an incident angle of optical flux, representative of the optical image, to the first deflecting optical element and an incident angle of the optical flux to the second deflecting element after it is reflected by the first deflecting optical element, so that the optical flux becomes linear polarizing light after being reflected by the second deflecting element, and the polarizing axis of at least one of the right and left eye polarizing plates is determined in accordance with the direction of the linear polarizing light.

9. An optometric apparatus according to claim 8, further comprising a subjective refractor capable of being moved to and away from a position close to the examinee's eye in the line of visual optical path of the examinee in looking at the optical image reflected by the second deflecting optical element, and wherein said first and second polarizing plates are arranged in said subjective refractor.

10. An optometric apparatus comprising:

a vision test chart displaying device for displaying a right eye polarizing test chart and a left eye polarizing test chart, wherein a polarizing light axis of the right eye polarizing test chart intersects with a polarizing light axis of the left eye polarizing test chart;

a plurality of mirrors for reflecting optical flux of the vision test charts to the examinee's eyes, the mirrors including a first mirror that reflects the optical flux to a second mirror that reflects the optical flux directly to the examinee's eyes;

a right eye polarizing plate and a left eye polarizing plate disposed in an optical path of the optical flux as it is reflected by the mirrors to the examinee's eyes, wherein a polarizing axis of the right eye polarizing plate intersects with a polarizing axis of the left eye polarizing plate;

wherein the polarizing light axes of the right eye polarizing test chart and the left eye polarizing test chart are determined based on an incident angle of the optical flux of the vision test charts to the first mirror and an incident angle of the optical flux of the vision test charts to the second mirror as it is reflected from the first mirror, so that the optical flux reflected by the plural mirrors becomes substantially linear polarizing light, and the polarizing light axes of the right and left eye polarizing plates are determined in accordance with the direction of the polarizing light.

11. An optometric apparatus according to claim 10, further comprising a subjective refractor capable of being moved to and away from a position close to the examinee's eye on the line of visual optical path between the second mirror optical element and the examinee's eyes, and said both polarizing plates being arranged in said subjective refractor.

12. An optometric apparatus comprising:

a housing;

a vision test chart displaying device provided internally within said housing;

an optical group, including a plurality of reflection-type optical elements, disposed within said housing, wherein the optical group repeatedly reflects an optical image of the vision test chart provided from said vision test chart displaying device;

a deflecting optical element for reflecting the optical image of the vision test chart reflected by said reflection-type optical elements outside said housing and in a direction toward the examinee's eyes; and turning means for turning said deflecting optical element to adjust the reflection of the optical image to the height of the examinee's eyes, the turning means including a control unit to control the turning angle of the deflecting optical element in accordance with an actuating signal.

13. An optometric apparatus according to claim 12, wherein said deflecting optical element comprises one or plural mirrors.

14. An optometric apparatus according to claim 12, further comprising a subjective refractor capable of being moved insertably to a position close to and in the line of vision of the examinee's eyes, and wherein said height detecting means for detecting the height of the examinee's eyes comprises a detecting means for detecting the height of said subjective refractor to indicate the height of the examinee's eyes.

* * * * *